(12) United States Patent
Traneus

(10) Patent No.: US 12,263,354 B2
(45) Date of Patent: Apr. 1, 2025

(54) COMPUTER PROGRAM PRODUCT AND COMPUTER SYSTEM FOR PLANNING AND DELIVERING RADIOTHERAPY TREATMENT AND A METHOD OF PLANNING RADIOTHERAPY TREATMENT

(71) Applicant: RaySearch Laboratories AB, Stockholm (SE)

(72) Inventor: Erik Traneus, Uppsala (SE)

(73) Assignee: RaySearch Laboratories AB, Stockholm (SE)

(*) Notice: Subject to any disclaimer, the term of this patent is extended or adjusted under 35 U.S.C. 154(b) by 485 days.

(21) Appl. No.: 17/627,389

(22) PCT Filed: Jul. 8, 2020

(86) PCT No.: PCT/EP2020/069229
§ 371 (c)(1),
(2) Date: Jan. 14, 2022

(87) PCT Pub. No.: WO2021/008964
PCT Pub. Date: Jan. 21, 2021

(65) Prior Publication Data
US 2022/0257976 A1    Aug. 18, 2022

(30) Foreign Application Priority Data
Jul. 15, 2019    (EP) .................... 19186236

(51) Int. Cl.
*A61N 5/10*    (2006.01)
(52) U.S. Cl.
CPC ........... *A61N 5/103* (2013.01); *A61N 5/1042* (2013.01); *A61N 5/1064* (2013.01); *A61N 2005/1087* (2013.01)

(58) Field of Classification Search
CPC .... A61N 5/103; A61N 5/1042; A61N 5/1064; A61N 5/1077; A61N 5/1031;
(Continued)

(56) References Cited

U.S. PATENT DOCUMENTS

2008/0260098 A1    10/2008    Al-Sadah et al.
2011/0049372 A1*    3/2011    Iseki .................... A61N 5/1043
                                                          250/363.01
(Continued)

FOREIGN PATENT DOCUMENTS

| CN | 107073284 A | 8/2017 |
| WO | WO-2012/070054 A1 | 5/2012 |
| WO | WO-2018/152302 A1 | 8/2018 |

OTHER PUBLICATIONS

Henry et al., "Development of an interlaced-crossfiring geometry for proton grid therapy," Acta Oncologica, Vo. 56, No. 11, pp. 1437-1443, 2017.

*Primary Examiner* — Kiet T Nguyen
(74) *Attorney, Agent, or Firm* — Faegre Drinker Biddle & Reath LLP

(57) ABSTRACT

A radiotherapy treatment plan for grid therapy in which a patient is radiated from a source of radiation with a set of spatially fractionated beams of charged particles such as protons, including varying the direction of each beam in the set of beams. Generating the plan comprises the steps of determining a first path through the patient to a first Bragg peak position and determining a second path through the patient, at least a part of the second path being directed at an angle from the first path to a first deflected Bragg peak position. The beam directions may be varied by means of magnetic fields or by varying the relative angle between the gantry and the patient.

16 Claims, 4 Drawing Sheets

(58) Field of Classification Search
CPC .. A61N 5/1048; A61N 5/1065; A61N 5/1071; A61N 5/1075; A61N 2005/1087; A61N 2005/1092
USPC ...................................................... 250/492.3
See application file for complete search history.

(56) References Cited

U.S. PATENT DOCUMENTS

| | | |
|---|---|---|
| 2013/0259198 A1 | 10/2013 | Alezra et al. |
| 2016/0175616 A1 | 6/2016 | Kwak et al. |
| 2017/0281981 A1* | 10/2017 | Mansfield ............ A61N 5/1077 |
| 2019/0022409 A1 | 1/2019 | Vanderstraten et al. |
| 2019/0022422 A1* | 1/2019 | Trail .................... H01J 35/065 |

* cited by examiner

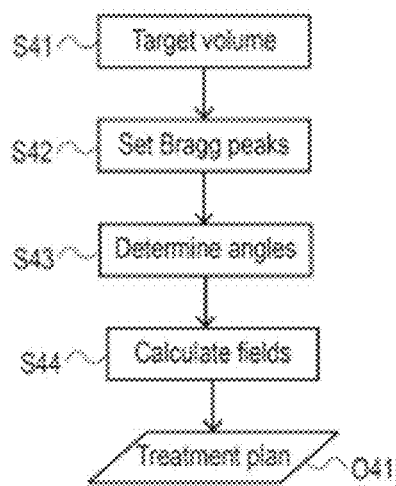 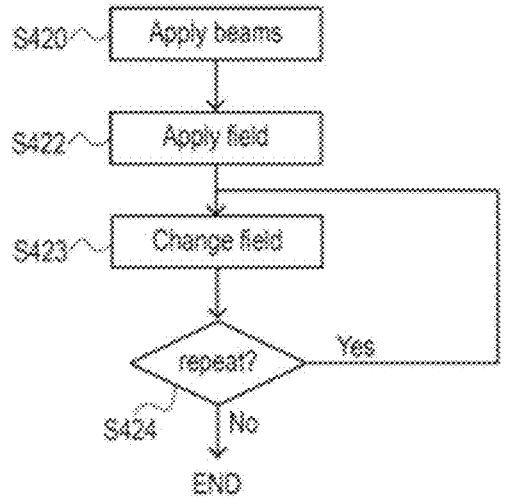
FIGURE 4a       FIGURE 4b
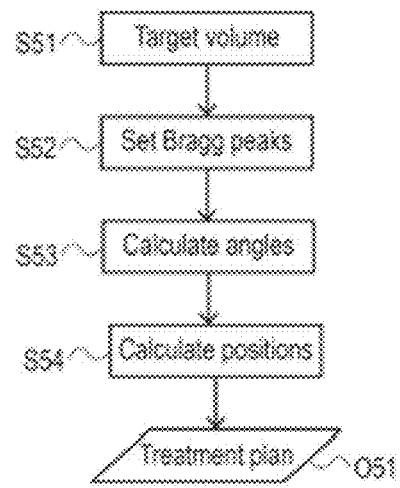 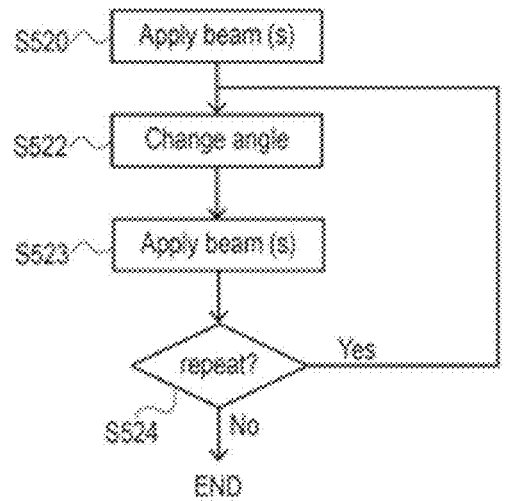
FIGURE 5a       FIGURE 5b

COMPUTER PROGRAM PRODUCT AND COMPUTER SYSTEM FOR PLANNING AND DELIVERING RADIOTHERAPY TREATMENT AND A METHOD OF PLANNING RADIOTHERAPY TREATMENT

CROSS REFERENCE TO RELATED APPLICATIONS

This application is a National Stage of International Application No. PCT/EP2020/069229, filed Jul. 8, 2020, and claims the benefit of European Patent Application No. 19186236.6, filed Jul. 15, 2019, the entire contents of each of which are incorporated herein by reference.

TECHNICAL FIELD

The present invention relates to a method, a computer program product and a computer system for radiotherapy treatment planning and to a system for delivery of radiotherapy treatment and a computer program product for controlling such delivery. More specifically, the invention relates to radiotherapy involving protons or other charged particles.

BACKGROUND

In conventional radiotherapy treatment, the radiation dose is normally divided into fractions, to minimize the damage to any tissue or organ that is not the target. A total dose of 60 Gy may for example be given in 30 fractions of 2 Gy each. A key issue in optimizing such treatment plans is ensuring that the target, typically a tumor, receives a sufficiently high dose while the dose to any surrounding tissue, in particular, any organ at risk, is kept low to minimize lasting damage. Presently, a lot of research and development is concerned with creating as precise treatment plans as possible and to create conformal dose distributions.

A somewhat different approach is grid therapy, in which a high dose, for example 15 or 20 Gy, is given in the shape of a grid, in one or few fractions. In other words, a spatially fractionated dose distribution is achieved. The grid may be achieved by means of geometrically spaced pencil beams, or by using an aperture block with a pattern of through holes that will let through a number of geometrically spaced beams. It has been known for a while that this form of treatment reduces the damage to the skin, since the unaffected portions of the skin between the beams will help the damaged portions heal. It has also been found that the same is true for the tissue beneath the skin, but not to the same degree for tumorous tissue. Therefore, grid treatment enables the administration of a single dose, high enough to cause a significant response in the tumor, while at the same time being tolerated by the patient. The whole target should receive at least a minimum dose, but the dose to the target does not have to be uniform. Of course, the grid treatment may also be administered more than once. Also, one or more grid treatments may be followed by surgery, and/or a number of conventional therapy fractions.

Grid therapy can be used with photon therapy or with charged particles, such as protons. For protons, the grid can be arranged by using physical collimators having slits or holes to divide the beam. Alternatively, a suitable pattern of uncollimated pencil beams may be applied.

In proton therapy, the particles will gradually slow down as they progress through the medium in which they are propagating. As they slow down their probability of interaction with the medium increases, leading to more energy being deposited. Where the particles stop, a high energy deposition peak, known as the Bragg peak, is the result. By planning the treatment so that the Bragg peaks will be positioned in the target, the dose can be controlled with a high precision. As the particles slow down they will also be scattered to a higher extent, so that the particle beam will be broadened somewhat towards the end of the path.

One challenge of grid therapy using protons or other charged particles, is to separate the beams laterally as much as is necessary to obtain the positive effect in the healthy tissue and still get a good dose coverage in the target. One way of overcoming this is to provide the grid treatment in two sessions, using different positions of the beams. If a grid block is used, this may be achieved by shifting the grid block between sessions. If pencil beams are used, each of the beams may be shifted for the second session to a position that was not covered in the first session.

One measure of quality in grid therapy is the peak to valley dose, which is the ratio between the dose value in the spots (the peak, or highest dose) and between the spots (the valley, or lowest dose). The peak to valley dose should be high in surrounding tissue and in particular in organs at risk, whereas in the target the dose should ideally be homogeneous, and high.

Thomas Henry, in his doctoral thesis: Interlaced proton grid therapy: development of an innovative radiation treatment technique, Department of Physics, Stockholm university, ISBN 978-91-7797-442-0, discusses these problems and investigates solutions using different beam widths. The aims were to maintain the grid pattern of the dose distribution while delivering a rather homogeneous dose to the target, with a high minimum dose. To do so, grids of proton beamlets incident from several directions were interlaced over the targeted volume so that together they would cover the whole target volume while maintaining the grid pattern in the tissue outside of the target. Henry et al.: Development of an interlaced-crossfiring geometry for proton grid therapy, Acta Oncologica, 2017, Vol. 56, No. 11, 1437-1443, discloses a method of obtaining homogeneous dose coverage shows examples of such interlaced grids with experimental data obtained in a laboratory setting.

SUMMARY

It is an object of the present invention to provide grid therapy using charged particles in which a sufficiently high and homogeneous dose to a target can be combined with a peak to valley dose that will spare surrounding tissue.

This object is achieved according to the present invention by a computer-implemented method of producing a radiotherapy treatment plan for grid therapy in which a patient is radiated from a source of radiation with a set of spatially fractionated beams of charged particles such as protons, including the steps, for each beam in the set of beams, of
  determining a first path through the patient to a first Bragg peak position,
  determining a second path through the patient, at least a part of the second path being directed at an angle from the first path to a first deflected Bragg peak position.

The main idea underlying the invention is to vary the trajectory of the protons traversing the body to broaden the area within the target that is covered by the beams, while maintaining the spacing in other parts of the patient's body. In this way, the points in which the beams enter the patient's body may be sufficiently far apart that the advantages to the skin and healthy tissue may be obtained, while the protons may still cover the whole of the target. According to the invention, the therapeutic window, that is, the practically attainable treatment that will harm the tumor and spare the surrounding tissue, including organs at risk, is effectively increased.

The trajectory may be varied in different ways. In a first embodiment, the trajectory is varied by varying the beam angle, for example by emitting beams from different gantry angles. In a second embodiment, the trajectory is varied by applying a magnetic field in such a way that some proton beams will be bent when traversing the patient. In the first embodiment, the first and second trajectories are realized by varying the beam angle from the source of radiation relative to the patient. Preferably, the beam angle is varied in such a way as to gradually change the beam angle to create a field of Bragg peaks.

In the second embodiment, deflection is achieved by means of at least one magnetic field. In this case, the first and second paths are realized by the following steps:

determining a desired particle energy to cause the first Bragg peak to be positioned within a target in the patient, determining a direction and strength of a first magnetic field to be applied to the beams to change the direction of the beam to follow the second path to the first deflected Bragg peak position.

Preferably in this case the step of determining a direction and strength of a second magnetic field to change the direction of the beam to follow a third path to a second deflected Bragg peak position, to allow for more than two different Bragg peak positions.

In one preferred embodiment, the magnetic field is varied while the beam is applied so as to gradually change the deflection of the beam to create a laterally smeared-out Bragg peak. This will result in a more even dose across the target.

The particles will have the highest energy when entering the patient, and will lose energy as they pass through the patient. Since the magnetic field will affect particles having a lower energy more than particles having a high energy, the beam will be bent more closer to the Bragg peaks, which should be placed in the target volume. When applying a magnetic field only for a part of the time, or changing the field direction, some beams will be bent within the target and some will not. In this way, the beams will spread to cover a larger area of within the target, while being kept narrow nearer to the entry point into the patient. Therefore, the advantages of grid therapy will be retained in the tissue outside of the target, while the target will be covered in a better way than in the prior art. In other words, a high peak to valley dose ratio can be obtained in risk organs while still treating the target effectively. Of course, two or more different magnetic fields may be applied to achieve even better spread of the beams. Preferably, a first magnetic field, and a second, opposite magnetic field are applied at different times, and for a part of the time, no magnetic field is applied.

The magnetic field strength should be selected to ensure a suitable bending angle of the beams, for example, +1 T, 0 T (that is, no magnetic field) and −1 T.

The magnetic fields may be generated in any suitable way. For example, three homogeneous axial fields may be applied. Alternatively, the field may be generated by a suitably short open solenoid. This will yield shallow fringe fields and a reduced maximum field volume at the center of the solenoid. This will result in a very good overlap of the Bragg peaks in the target with reduced deflection away from the target.

Magnetic fields are commonly used in the field of radiotherapy for shaping and directing beams before they are emitted towards the patient. The invention, in some embodiments, proposes to use magnetic fields to direct beams within the patient.

The invention also relates to a computer program product for planning a radiotherapy treatment plan, which when performed in a computer, will cause the computer to perform the planning method according to the above. The computer program product is typically stored on a memory device, such as a non-transitory memory device. The invention also relates to a computer system comprising a processor and a program memory, the program memory comprising such a computer program product.

The invention also relates to the delivery of a radiotherapy treatment plan. Hence, the invention relates to a computer program product for controlling the delivery of radiotherapy treatment from a delivery apparatus to a patient, said treatment involving radiating the patient with a set of spatially fractionated beams of charged particles such as protons, comprising computer-readable code means which when run in a processor of an apparatus for providing radiotherapy treatment will cause the apparatus to perform the following steps, in any desired order:

radiating the patient with the set of spatially fractionated beams so that each beam will follow a first path through the patient to a first Bragg peak position, radiating the patient with the set of spatially fractionated beams so that each beam will follow a second path through the patient to a displaced Bragg peak position.

The invention also relates to an apparatus for providing radiotherapy treatment to a patient, said apparatus means or generating a set of spatially fractionated beams of charged particles such as protons, said apparatus being arranged to vary the path of each beam within the patient in such a way that the beams' doses will be spatially fractionated while passing through healthy tissue of the patient and overlap within a target in the patient, the apparatus further comprising processing means arranged to control the device and a program memory comprising a computer program product for controlling the delivery of radiotherapy treatment as discussed above.

If the deflection of the beam is achieved by means of a magnetic field, the delivery apparatus comprises a device for generating a magnetic field that will affect the path of the particles within the patient, comprising the steps of radiating the patient with the set of spatially fractionated beams while applying a first magnetic field arranged to bend the paths of the beams.

radiating the patient with the set of spatially fractionated beams while applying no magnetic field or a second magnetic field arranged to bend the paths of the beams.

In this case, the apparatus comprises a device arranged to generate a magnetic field for modifying the paths of the particles in each beam within the patient. The device is preferably arranged to generate a magnetic field that will bend the path of the particles in each beam near their Bragg peaks. Advantageously, the device is arranged to vary the strength and/or direction of the magnetic field.

If the deflection of the beam is achieved by varying the beam angle, the delivery apparatus is arranged to vary the beam angle of the spatially fractionated beams so that the beams' doses will be spatially fractionated while passing through the skin of the patient and overlap within the target. In this case, the apparatus is arranged to vary the direction of each beam by tilting the gantry and/or the position and/or orientation of the patient.

BRIEF DESCRIPTION OF THE DRAWINGS

The invention will be described in more detail in the following, by way of example and with reference to the appended drawings, in which

FIGS. 4a and 4b are flow charts of a treatment planning method and a treatment delivery method, respectively, according to the first embodiment.

FIGS. 5a and 5b are flow charts of a treatment planning method and a treatment delivery method, respectively, according to the second embodiment.

DETAILED DESCRIPTION

Figure 1:
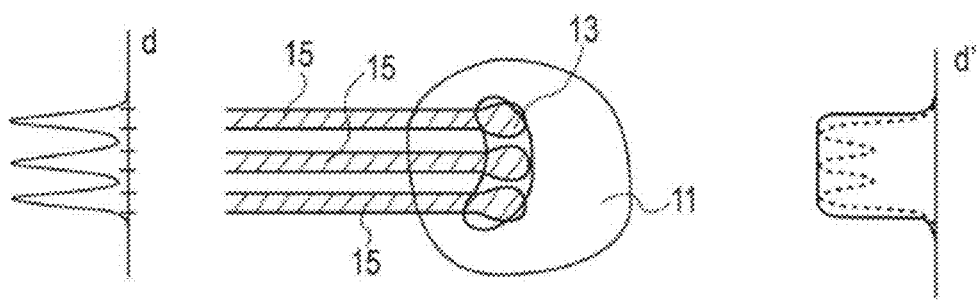
FIG. 1 illustrates the general principle of grid therapy.

FIG. 1 illustrates the general principle of grid therapy, simplified in two dimensions. A section through a patient 11 is shown comprising a tumor 13. In this example, three beams 15, spaced apart, are directed at the tumor 13. As will be understood, a grid pattern for clinical use will be three-dimensional and include a higher number of beams. The grid can be created in any suitable way, for example, by use of a block with openings where the beams are allowed to pass, or by pencil beams.

On the left in FIG. 1 there is a simplified diagram showing the dose profile d on the skin of the patient resulting from the beams. There are three peaks, corresponding to the positions of the beams, with distinct valleys between them. The beams will traverse the patient's body, leaving the area between the beams substantially unaffected. On the right there is another diagram showing the dose profile d' in the target as a dashed line. As can be seen, it has the same three peaks as the dose profile d, but somewhat lower peak to valley ratio. An ideal dose profile, showing a high and homogeneous dose to the target, is shown as a solid line for comparison.

Figure 2A:
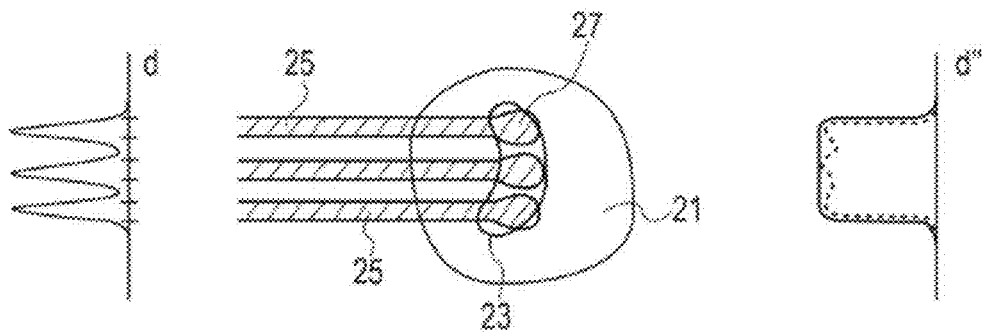
FIGS. 2a-2e illustrate a first embodiment of the invention.

FIG. 2a illustrates a similar situation involving a patient 21 having a tumor 23. In this case the beams 25 are proton beams, spaced apart and arranged so that their Bragg peaks will be located inside of the tumor. As mentioned in the introduction, and indicated in FIG. 2a, each beam broadens towards the Bragg peak, that is, the end 27 of the beam path, so that the coverage of the tumor will be more homogeneous than the coverage of the traversed tissue. Again, on the left in FIG. 2a there is a simplified diagram showing the dose profile d on the skin of the patient resulting from the beams, with similar peaks as for FIG. 1

Figure 2B:
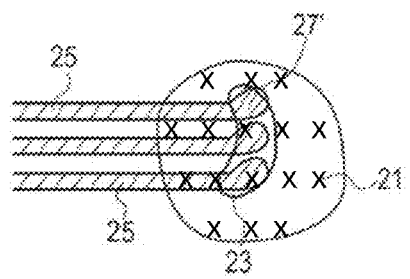

FIG. 2b illustrates a similar situation as in FIG. 2a, the only difference being that a first magnetic field is applied over the patient, to cause the protons in the beams 25 to change direction. The magnetic field is shown as a matrix of crosses, indicating that the field lines are directed away from the observer. As explained above, the directions will change more for particles having a lower energy so that the beams 25 will be bent close to the Bragg peaks, that is, within the tumor. In FIG. 2b, the beams 25 are bent upwards in the drawing. Of course, the beams 25 may be bent in any suitable direction, depending on the direction of the magnetic field. As the beams 25 are already broadened near the Bragg peaks, the resulting beam shapes 27' will be broadened and bent at the end of each beam, the direction and magnitude of the change of direction being controlled by the direction and strength of the magnetic field.

Figure 2C:
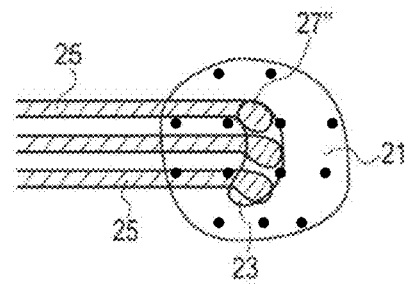

FIG. 2c illustrates a similar situation as in FIG. 2b, but with a second magnetic field, which is different from the first magnetic field. In FIG. 2c, the magnetic field has been inversed compared to the one in FIG. 2b. The magnetic field is shown as a matrix of dots, indicating that the field lines are directed towards the observer. The direction of the protons will change in the opposite direction from that shown in FIG. 2b causing a broadened beam shape that bends downwards in the Figure towards the end 27". The resulting patterns within the tumor 23 in FIGS. 2a, 2b, 2c, 2d, and 2e will complement each other, enabling all parts of the tumor 23 to be covered by means of the same distinct beams. As will be understood, by applying radiation in three portions, without a magnetic field, and with the first and second magnetic field applied, the coverage of the tumor 23 can be improved, while maintaining the grid pattern and its advantages in the patient's other tissues. The three portions may be applied in one operation, by changing the magnetic field during a treatment fraction.

Figure 2D:
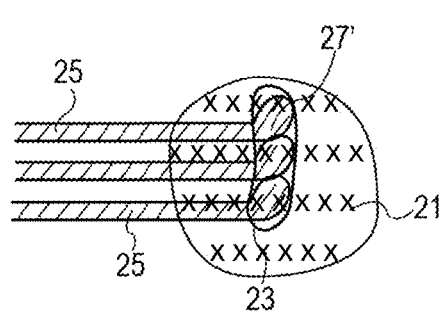
Figure 2E:
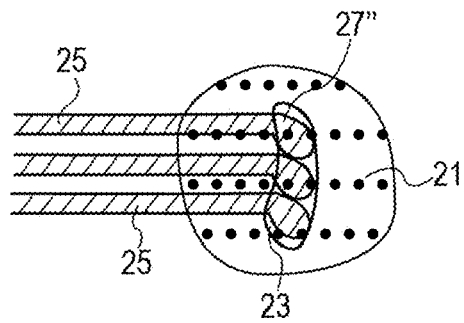

FIG. 2d illustrates the same situation as in FIG. 2b, with a stronger magnetic field, indicated by a shorter distance between the crosses. As can be seen, the deflection upwards is greater than in FIG. 2b. FIG. 2e illustrates the same situation as in FIG. 2c, with a stronger magnetic field, indicated by a shorter distance between the crosses. As can be seen, the deflection downwards is great than in FIG. 2c.

On the right in FIG. 2a there is a diagram showing a realistic dose profile d" which is the sum of the beams within the tumor 23 according to FIGS. 2a, 2b, 2c, 2d, and 2e. The realistic dose profile is shown as a dashed line. An ideal dose profile is shown as a solid line for comparison. The ideal dose profile shows a high and homogeneous dose within the whole tumor. As can be seen, the realistic dose profile is closer to the ideal dose profile, with much less pronounced peaks and valleys than the dose profiles d and d'.

As will be understood, the combined use of two opposite magnetic fields and no magnetic field is just an example. There may be only one magnetic field, or several different magnetic fields, combined with no magnetic field. Alternatively, two or more magnetic fields that are different from each other but not necessarily opposite from each other may be applied. In this way, the magnetic fields may be used to affect the beams to cover the whole tumor in the best possible way while keeping the advantages associated with grid treatment in the reduced harm to the patient's skin and other tissues.

The magnetic field may be generated in any suitable way but preferably in a way that enables its strength and direction to be controlled. One preferred way is to apply homogenous axial fields. A suitable alternative is to use a short open solenoid.

Figure 3A:
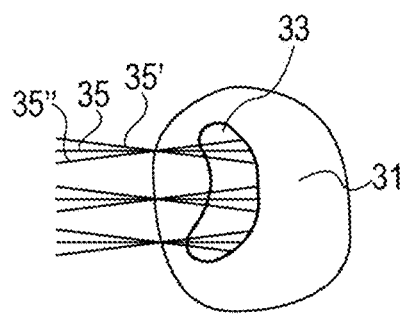
FIGS. 3a-3b illustrates a second embodiment of the invention.
Figure 3B:

FIG. 3a illustrates an alternative embodiment, in which the increased coverage of the tumor is achieved by changing the beam direction, for example, by tilting the gantry. Again, a section through a patient 31 is shown, including a tumor 33. For simplicity of presentation, again, three solid beams 35 are shown to enter the patient horizontally, each resulting in a Bragg peak position in the patient. Each of the beam also has two corresponding beams 35' and 35", shown as lines and with the same entry point but slightly tilted upwards and downwards, respectively, resulting in Bragg peak positions that will be referred to here as deflected positions. As can be seen, the beams will be spaced apart at the points of entry and along their paths through the patient, but will overlap within the tumor 33. The angle between the horizontal beam and each of the corresponding beams is selected to maintain beam spacing at entry and ensure good dose coverage in the whole target. A suitable angle may be determined by common trigonometry. For example, assuming that the distance to the target is 10 cm, the spot separation is 1 cm, and the system is set up to tilt each beam first to one side of the spot and then to the opposite side, the angle should be chosen such that the deflected positions are placed at ⅓ of the spot separation so that the spots and the deflected positions will be equidistant. In this example, the angle becomes arcsin (0.33/10)=1.9 degrees. The general equation for the angle α can be expressed as $$\alpha = \arcsin\frac{s}{d} \quad (1)$$

where s is the desired distance from the spot to the deflected position, in this case ⅓ cm, and d is the distance to the target. FIG. 3b shows an example of angle α, representing the tilt of the beam, as a function of the distance d to the target and the distance s from the spot to the deflected position. The deflected positions of the respective spots are marked as x' and are placed at a distance s from the spot x on either side of the spot x.

While FIG. 3 shows each beam entering from three different angles and rotating only in the plane of the drawing, it would of course be possible to make the beam enter from only two different angles, or from four or more different angles, and also to vary the angle in three dimensions. Instead of varying the gantry angle, the couch may be rotated to achieve the same effect. For more degrees of freedom both the gantry and the couch may be rotated or tilted. If a grid block is used, care must be taken so that the direction of the block allows the beam to pass through the openings of the block. If the block is tilted too much with respect to the beam direction, the beam may be stopped completely, or at least to a too high degree, by the block. This can be avoided by fixing the block to the gantry so that the angle between the beam and the block is fixed. If the beams from different angles are arranged to intersect at the entry point into the patient, as shown in FIG. 3, a block placed at the patient's outline will not have to be tilted to let the beams through, or the required tilting angle will be smaller.

FIG. 4a is a flow chart of a possible method of planning a radiotherapy treatment according to the first embodiment the invention. In a first step S41, a target volume is defined, that is, the volume that should be affected by the radiotherapy. In a second step S42, suitable positions of Bragg peaks are determined to provide suitable coverage of the volume and the corresponding beam energies are set. Steps S41 and S42 may be performed in ways well known in the art. In a third step S43, one or more angles that the beams should be deflected are determined. The angles are calculated or selected to provide Bragg peaks between the Bragg peak positions determined in step S42. The angles may, for example, be calculated according to Eq (1). Next, in step S43, the magnetic field or fields that need to be applied to the beams to deflect them by the angles determined in step S43 are calculated or determined in some other way. The output O41 from this procedure is a treatment plan including a set of beams having specified energy levels, and one or more magnetic fields to be applied to deflect the beams.

In the example shown, each beam is assumed to be deflected in two opposite directions (up and down as seen in the drawings). Of course, the directions can be selected as is found suitable. It is also possible to create only one deflected beam, or more than two. For example, four beams deflected orthogonally around the untilted beam may be applied.

The magnetic fields may be generated in any suitable way. It may be possible in step S43 to vary both the strength and the direction of the magnetic field, or only the strength. If enabled by the system, the magnetic field can be varied while the beam is applied, so that instead of for example three distinct Bragg peaks the beam can be made to deposit energy in an area around the Bragg peak position determined in step S42. Instead of a number of distinct beam directions, the beam may be varied to form a conical shape.

FIG. 4b is a general flow chart of a treatment delivery method according to an embodiment of the invention. In a first step S420, a set of proton beams are applied to a patient with no magnetic field applied. The proton beams will follow an essentially straight line within the patient until the end of the path. In step S422, a first magnetic field is applied to the proton beams, with the result that the proton beams are caused to bend in a first direction towards the end of their beam paths. In step S423, a second magnetic field is applied to the proton beams, to cause the proton beams to bend in a second direction towards the end of their beam path. In a decision step S424, it is decided if yet another magnetic field is to be applied to cause the proton beams to bend in a further direction. If yes, the procedure returns to step S423, as indicated in FIG. 4, or to step S422; if no, the procedure ends. If pencil beam scanning is used, each beam can be affected individually; if a grid block is used to shape the beams all beams will be affected in the same way.

The magnetic fields applied in steps S422 and S423 are different from each other to cause additional spreading of the protons within the target. They may be equal but opposite, or may differ in any other suitable way, including direction and strength. The magnetic fields may have the same or opposite directions but different strengths, but they may also have different directions if the equipment generating the field can be rotated relative to the proton beams. It would also be possible to include only one of the steps S422 and S423, to apply only one magnetic field. Of course, step S420 could instead be omitted, so that there was no step with no magnetic field affecting the beam. If the magnetic field is arranged to vary continuously, each Bragg peak may be smeared out laterally.

The magnetic field will, for practical reasons, typically extend outside of the patient's body and will therefore affect the beam even outside of the patient, but less with increasing distance from the patient. As discussed above, care must be taken that the grid block, if present, does not block the beams. For this embodiment, it is suitable, but not necessary, to place the grid block close to the patient and at a fixed angle independent from the gantry angle.

FIG. 5a is a flow chart of a possible method of planning a radiotherapy treatment according to the second embodiment the invention.

In a first step S51, a target volume is defined, that is, the volume that should be affected by the radiotherapy. In a second step S52, suitable positions of Bragg peaks are determined to provide suitable coverage of the volume and the corresponding beam energies are set. Steps S51 and S52 may be performed in ways well known in the art. In a third step S53, one or more angles that the beams should be deflected are determined. The angles are calculated, for example according to Eq. (1) above, or selected in some other way to provide Bragg peaks between the Bragg peak positions determined in step S42. Next, in step S43, the gantry angles, or relative positions between gantry and couch that are needed to achieve these angles are determined. The output O41 from this procedure is a treatment plan including a set of beams having specified energy levels, and one or more gantry angles and/or gantry/couch positions to be applied to deflect the beams.

FIG. 5b is a flow chart of a possible treatment delivery method according to the second embodiment. In a first step S520, one or more beams of charged particles are applied. In a second step S522, the incident angle of the one or more beams is changed and in a third step S523 the beams are applied again. Step S524 is a decision step to determine if another incident angle is to be used for the beams. If yes, the procedure returns to step S522, if no, the procedure ends.

Figure 6:
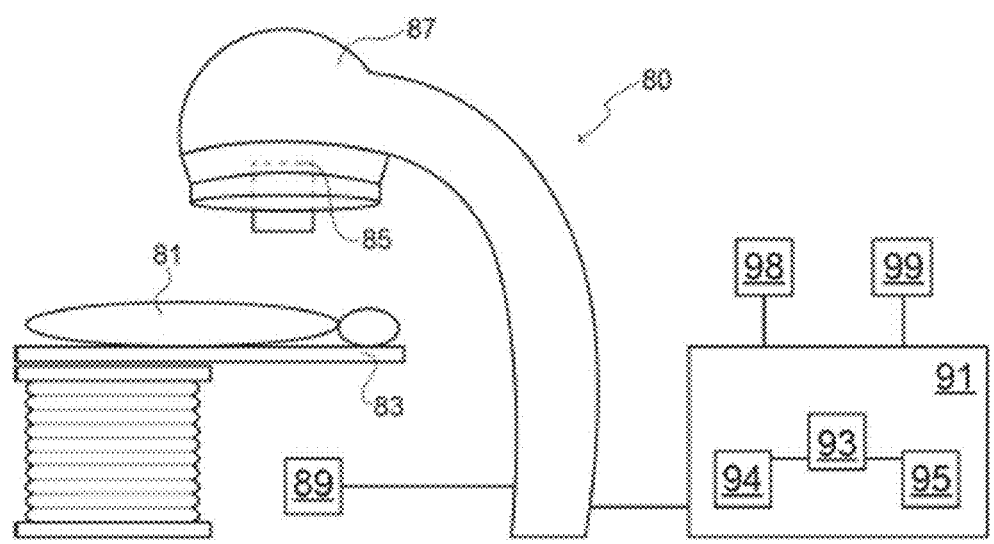
FIG. 6 shows an example of a general dose delivery system that may also be used for treatment planning.

FIG. 6 is an overview of a system 80 for radiotherapy treatment and/or treatment planning. As will be understood, such systems may be designed in any suitable way and the design shown in FIG. 6 is only an example. A patient 81 is positioned on a treatment couch 83. The system comprises an imaging/treatment unit having a radiation source 85 mounted in a gantry 87 for emitting radiation towards the patient positioned on the couch 83. Typically, the couch 83 and the gantry 87 are movable in several dimensions relative to each other, to provide radiation to the patient as flexibly and correctly as possible. These parts and their functions are well known to the skilled person. A number of passive devices provided to shape the beam laterally and in depth are typically present and will not be discussed in more detail here. Means are arranged for providing a grid of beams, for example in the form of a grid block, or means for providing pencil beams. In this example the system also comprises means 89 for generating a magnetic field that will affect the path of the particles of the beam inside the patient's body and means for modifying the magnetic field. The means 89 for generating the magnetic field may be any suitable means, such as one or more magnets, or one or more coils. The modifying means can be any type of means, for example arranged to modify the position and direction of the magnets or coils, and to control the current through the coils. The system also comprises a computer 91 which may be used for radiotherapy treatment planning and/or for controlling radiotherapy treatment. As will be understood, the computer 91 may be a separate unit not connected to the imaging/treatment unit.

The computer 91 comprises a processor 93, a data memory 94, and a program memory 95. Preferably, one or more user input means 98, 99 are also present, in the form of a keyboard, a mouse, a joystick, voice recognition means or any other available user input means. The user input means may also be arranged to receive data from an external memory unit.

The data memory 94 comprises clinical data and/or other information used to obtain a treatment plan. Typically, the data memory 94 comprises one or more patient images to be used in treatment planning according to embodiments of the invention. For the embodiments in which a magnetic field is used to change the beam path, as illustrated in FIGS. 2a-2c and 4, field maps depicting possible magnetic fields must be available, for example, in the data memory 94. The field maps are input to the particle transport simulation being part of the dose computation. The program memory 95 holds at least one computer program arranged to cause the processor to perform a treatment planning method, for example, according to FIG. 4a or 5a and/or a computer program arranged to make the computer control the radiotherapy treatment of a patient, for example, according to FIG. 4b or 5b.

As will be understood, the data memory 94 and the program memory 95 are shown and discussed only schematically. There may be several data memory units, each holding one or more different types of data, or one data memory holding all data in a suitably structured way, and the same holds for the program memories. One or more memories may also be stored on other computers. For example, the computer may be arranged to perform only one of the methods, there being another computer for performing the optimization.

The invention claimed is:

1. A computer-implemented method of producing a radiotherapy treatment plan for grid therapy in which a patient is irradiated from a source of radiation with a set of spatially fractionated beams of charged particles the method comprising, for each beam in the set of beams:
   determining a first path through the patient to a first Bragg peak position; and
   determining a second path through the patient, at least a part of the second path being directed at an angle from the first path to a first deflected Bragg peak position.

2. The method according to claim 1, wherein the first and second paths are realized by the following steps:
   determining a desired particle energy to cause the first Bragg peak to be positioned within a target in the patient; and
   determining a direction and strength of a first magnetic field to be applied to the beams to change the direction of the beam to follow the second path to the first deflected Bragg peak position.

3. The method according to claim 2, further comprising the step of determining a direction and strength of a second magnetic field to change the direction of the beam to follow a third path to a second deflected Bragg peak position.

4. The method according to claim 2, comprising the step of varying the first magnetic field while the beam is applied so as to gradually change a deflection of the beam to create a laterally smeared-out Bragg peak.

5. The method according to claim 1, wherein the first and second paths are realized by varying the beam angle from the source of radiation relative to the patient.

6. The method according to claim 5, wherein the beam angle is varied in such a way as to gradually change the beam angle to create a field of Bragg peaks.

7. A computer program product for planning a radiotherapy treatment plan, which when performed in a computer, will cause the computer to perform the method according to claim 1.

8. A computer system comprising a processor and a program memory, the program memory comprising the computer program product according to claim 7.

9. A computer program product for controlling a delivery of radiotherapy treatment from a delivery apparatus to a patient in the form of grid therapy, said treatment involving irradiating the patient with a set of spatially fractionated beams of charged particles such as protons, comprising non-transitory computer-readable code means which when run in a processor of an apparatus for providing radiotherapy treatment will cause the apparatus to perform the following steps, in any desired order:
   irradiating the patient with the set of spatially fractionated beams so that each beam will follow a first path through the patient to a first Bragg peak position; and
   irradiating the patient with the set of spatially fractionated beams so that each beam will follow a second path through the patient to a deflected Bragg peak position.

10. The computer program product according to claim 9, wherein the delivery apparatus comprises a device for generating a magnetic field that will affect the path of the particles within the patient, comprising the steps of:

irradiating the patient with the set of spatially fractionated beams while applying a first magnetic field arranged to bend the paths of the beams; and irradiating the patient with the set of spatially fractionated beams while applying the first magnetic field or a second magnetic field arranged to bend the paths of the beams.

11. An apparatus for providing radiotherapy treatment in the form of grid therapy to a patient, said apparatus means or generating a set of spatially fractionated beams of charged particles such as protons, said apparatus being arranged to vary the path of each beam within the patient in such a way that the doses of the beams will be spatially fractionated while passing through healthy tissue of the patient and overlap within a target in the patient, the apparatus further comprising processing means arranged to control the device and a program memory comprising the computer program product according to claim 10.

12. The apparatus according to claim 11, further comprising a device arranged to generate a magnetic field for modifying the paths of the particles in each beam within the patient.

13. The apparatus according to claim 11, wherein the device is arranged to generate a magnetic field that will bend the path of the particles in each beam near their Bragg peaks.

14. The apparatus according to claim 13, wherein the device is arranged to vary the strength and/or direction of the magnetic field.

15. The apparatus according to claim 11, wherein the apparatus is arranged to vary the direction of each beam by tilting a gantry and/or a position and/or an orientation of the patient.

16. The computer program product according to claim 9, wherein the delivery apparatus is arranged to vary a beam angle of the spatially fractionated beams so that the doses of the beams will be spatially fractionated while passing through a skin of the patient and overlap within the target.

* * * * *